(12) United States Patent
Shah

(10) Patent No.: US 8,652,498 B2
(45) Date of Patent: Feb. 18, 2014

(54) PESTICIDAL COMPOSITION

(71) Applicant: Bimal Deepak Shah, Mumbai (IN)

(72) Inventor: Bimal Deepak Shah, Mumbai (IN)

( * ) Notice: Subject to any disclaimer, the term of this patent is extended or adjusted under 35 U.S.C. 154(b) by 0 days.

(21) Appl. No.: 13/621,881

(22) Filed: Sep. 18, 2012

(65) Prior Publication Data

US 2013/0071460 A1   Mar. 21, 2013

(30) Foreign Application Priority Data

Sep. 19, 2011  (IN) .......................... 2650/MUM/2011

(51) Int. Cl.
*A01N 25/34*   (2006.01)
*A01N 25/00*   (2006.01)

(52) U.S. Cl.
USPC ............................. 424/408; 424/405; 424/705

(58) Field of Classification Search
USPC ......................................... 424/405, 408, 705
See application file for complete search history.

(56) References Cited

U.S. PATENT DOCUMENTS

| | | | |
|---|---|---|---|
| 2005/0076686 A1* | 4/2005 | Tidow et al. ...................... 71/54 |
| 2009/0208423 A1* | 8/2009 | Jadhav et al. ............... 424/10.31 |

FOREIGN PATENT DOCUMENTS

| | | | | |
|---|---|---|---|---|
| WO | WO2012101659 | * | 8/2012 | ............ A01N 59/02 |

* cited by examiner

*Primary Examiner* — Rachael E Bredefeld
(74) *Attorney, Agent, or Firm* — Harris, Shelton, Hanover & Walsh; Susan B. Fentress

(57) ABSTRACT

The present invention relates to an agricultural composition comprising sulphur in the range from 20% to 80% of the total composition, a chloronicotinyl compound in the range from 0.7% to 25% of the total composition, a pyrethroid compound in the range from 0.75% to 10% of the total composition and at least one agrochemically acceptable excipient

8 Claims, No Drawings

PESTICIDAL COMPOSITION

This application was created under a joint research agreement between: Bimal Deepak Shah andDeepak Pranjivandas Shah pursuant to 35 USC 103 (c) of the CREATE ACT.

CROSS REFERENCE TO RELATED APPLICATIONS

This application claims priority to Indian application no. 2650/MUM/2011 filed Sep. 19, 2011 under 35 U.S.C. 119 (a).

BACKGROUND OF THE INVENTION

1. Field of the Invention

The present invention relates to an agricultural composition comprising an effective amount of sulphur; an effective amount of a chloronicotinyl compound; an effective amount of a pyrethroid compound and at least one agrochemically acceptable excipient. The invention further relates to a process of preparing the agricultural composition.

2. Description of the Related Art

Compositions comprising chloronicotinyl compounds and pyrethroid compounds have been known in the art. However, the use of chloronicotinyl and pyrethroid compounds has more than doubled in the last few years, due to development of resistance against these pesticides.

Also, the biological properties of these mixtures of known compounds are not entirely satisfactory in the areas of pest control, phytotoxicity, and environment and user exposure.

As regards pesticide activity, in particular for the protection of crops, one of the problems at the heart of the research studies carried out in this technical field is the improvement of performances, in particular in terms of biological activity and in particular in terms of maintaining such an activity over time.

Also, another problem encountered concerns the need to have available pest control agents which are effective against a broad spectrum of pests, e.g. both animal pests and harmful fungi.

Further demands on pesticidal compositions are to reduced phytotoxicity, reduced dosage, substantial broadening of spectrum and increased safety, to name a few.

SUMMARY OF THE INVENTION

The inventors have surprisingly discovered that an agricultural composition comprising sulphur in the range from 20% to 80% of the total composition, chloronicotinyl compound in the range from 0.7% to 25% of the total composition and pyrethroid compound in the range from 0.75% to 10% of the total composition and at least one agrochemically acceptable excipient, demonstrated excellent synergistic pest control effect.

The pesticidal compositions offer a broad spectrum of protection, demonstrate synergistic effect against various pests, addresses the concerns of resistance, improve foliage, improve rainfastness and in various instances, improve crop yield and grain quality. The compositions disclosed herein, also serve as an intervention application between very specific actives, which alone are likely to lead to resistance in areas of epidemic and high frequency of pesticidal application.

It has also been found that the compositions show markedly enhanced action against pests compared to the control rates that are possible with the individual compounds.

DETAILED DESCRIPTION

In describing the embodiments of the invention, specific terminology is resorted for the sake of clarity. However, it is not intended that the invention be limited to the specific terms so selected and it is to be understood that each specific term includes all technical equivalents that operate in a similar manner to accomplish a similar purpose.

The present invention relates to an agricultural composition comprising sulphur in the range from 20% to 80% of the total composition; chloronicotinyl compound in the range from 0.7% to 25% of the total composition; and pyrethroid compound in the range from 0.75% to 10% of the total composition and at least one agrochemical excipient.

According to an embodiment, the chloronicotinyl compound can be selected from a group comprising of acetamiprid, thiamethoxam, imidacloprid, thiacloprid, dinetofuran or chlothianidin or salts thereof.

According to an embodiment, the pyrethroid. compound can selected from a group consisting of acrinathrin, bifenthrin, cyfluthrin, cypermethrin, cyhalothrin, deltamethrin, fenvalerate, fenpropathrin or salts thereof.

According to a further embodiment, the agricultural composition can be in the form of water dispersible granules (WDG) or pellets, emulsion concentrates (EC), wettable powders (WP), dusting powders, suspension concentrates (SC), suspo-emulsions, microemulsions, capsulated suspension (CS), emulsions for seed treatment and combination thereof.

Water dispersible granules can be defined as a pesticide formulation consisting of granules to be applied after disintegration and dispersion in water. As described herein, "WG" or "WDG" refer to water dispersible granules.

Suspension concentrate can be defined as a stable suspension of pesticide in a fluid usually intended for dilution with water before use. As described herein, "SC" refers to suspension concentrates.

According to an embodiment, the agricultural composition can comprise sulphur, imidacloprid and lambda cyhalothrin. According to a further embodiment, the agricultural composition can comprise 20%-60% sulphur, 1.25%-15% imidacloprid, 0.75%-10% lambda cyhalothrin and at least one agrochemically acceptable excipient.

According to an embodiment, the agricultural composition can comprise sulphur, acetamiprid and deltamethrin. According to a further embodiment, the agricultural composition can comprise 40-80% sulphur, 1%-5% acetamiprid, 0.7%-5% deltamethrin and at least one agrochemically acceptable excipient.

According to an embodiment, the agricultural composition can comprise sulphur, acetamiprid and lambda cyhalothrin. According to a further embodiment, the composition can comprise 25%-65% sulphur, 0.7%-10% acetamiprid, 0.75%-10% lambda cyhalothrin and at least one agrochemically acceptable excipient.

According to an embodiment, the agricultural composition can comprise sulphur, thiamethoxam and lambda cyhalothrin. According to a further embodiment, the composition can comprise an effective amount of 25%-65% sulphur, 2.5%-12.5% thiamethoxam, 1%-10% lambda cyhalothrin and at least one agrochemically acceptable excipient.

According to yet another embodiment, at least one agrochemically acceptable excipient can comprise wetting agents, dispersing agents, emulsifiers, binding agents, sticking agents, fillers, diluents, solvents, coating agents and stabilizers. However, those skilled in the art will appreciate that it is possible to utilize additional agrochemically acceptable excipients without departing from the scope of the present invention. The agrochemically acceptable excipient can be in the range from 4% to 60% of the total weight of the composition.

Surfactants which can be used as wetting agents and/or dispersing agents include sulfosuccinates, naphthalene sulfonates, sulfated esters, phosphate esters, sulfated alcohol, alkyl benzene sulfonates polycarboxylates, naphthalene sulfonate condensates, phenol sulfonic acid condensates, lignosulfonates, methyl oleyl taurates and polyvinyl alcohols,. However, those skilled in the art will appreciate that it is possible to utilize other surfactants known in the art without departing from the scope of the invention.

Fillers which can optionally be used include diatomaceous earth, kaolin, precipitated silica, attapulgite and perlite. In most cases the compositions can be enabled without the use of fillers. However, those skilled in the art will appreciate that it is possible to utilize other fillers known in the art without departing from the scope of the invention.

According to yet another embodiment, the invention further relates to a process of preparing the agricultural composition comprising an effective amount of a chloronicotinyl compound; an effective amount of a pyrethroid compound and at least one agrochemical excipient.

According to an embodiment composition comprising sulphur and neonicotinoid insecticide along with synthetic pyrethroid insecticide can be prepared by various processes.

For instance water dispersible granular compositions can be obtained by initially mixing requisite amount of sulphur and the respective amount of neonicotinoid insecticide and pyrethroid insecticide in a dispersion of required additives such as wetting agents, dispersing agents, emulsifiers and fillers. The slurry is then wet milled using an appropriate mill, like a bead mill, to obtain an average particle size of less than 50 microns, preferably less than 15 microns, preferably 1 to 3 microns. The mill base thus obtained is granulated in an appropriate spray drier with an out let temperature around 70 degree C. followed by sieving to remove the under sized and oversized particles, to obtain the respective WG formulations.

Alternately, wettable powder compositions of sulphur and these insecticides can be prepared by first blending requisite amount of Sulphur, neonicotinoid insecticide and pyrethroid insecticide and the required additives such as wetting agents, dispersing agents and fillers. The mixture is then micronised using a suitable mill like fluid energy mill; to an average particle size of less than 50 microns, preferably less than 15 microns, preferably 4 to 6 microns to get the WP formulation comprising sulphur, neonicotinoids and synthetic pyrithroids in combination.

Alternately SC compositions of sulphur and the respective insecticides can also be prepared as follows. Mill base, having the desired average particle size (between 0.8 microns to 5 microns) is prepared by milling the required amounts of sulphur technical (99% purity), and the requisite amounts of respective insecticides belonging to neonicotinoid and synthetic pyrethroid groups in a dispersion of requisite amounts of additives such as sodium naphthalene sulfonate condensate, sodium phenol sulfonate condensate and sodium lignin sulfonate in required quantity of water and propylene glycol. 2% Dispersion of xanthum gum (eg. Rhodopol) in water containing 0.5% 1,2- Benzisothiazolin-3-one (eg. Proxel) is then added to the mill base and mixed thoroughly to get SC formulations of the desired combination of Sulphur and insecticides.

Alternately ZC compositions of sulphur, neonicotinoid and pyrethroid may be prepared as follows. Suspention concentrate (SC) compositions of sulphur and the neonicotinoid insecticides is prepared by milling a mixture of requisite amount of sulphur technical and the neonicotinoid in a dispersion of requisite amounts of surfactants and filler in a required quantity of water containing the anti freezing agent and having an average particle size of less than 2 microns(step 1). A Capsulated suspension (CS) formulation is prepared separately by first dispersing the solution of requisite quantity of pyrethroid, the monomer and the polymeric surfactant in solvent in a dispersion of nonionic emulsifier in water. After pH adjustment the dispersion is kept under stirring at 50 degree C. for about two hours and finally the dispersion is neutralised to get the CS of pyrethroid (Step 2). Finally the SC of sulphur and neonicotinoid obtained in Step 1, the CS obtained in Step 2 and the requisite amount of Xanthum gel are mixed to get the ZC formulation of Sulphur, neonicotinoid and pyrethroid.

According to a still further embodiment, the invention further relates to a method of application of the agricultural composition to crops and plants.

Surprisingly, In particular, it has now been observed that, the pesticidal activity of the composition comprising sulphur in the range from 20% to 80% of the total composition, chloronicotinyl compound in the range from 0.7% to 25% of the total composition, pyrethroid compound in the range from 0.75% to 10% of the total composition and at least one agrochemically acceptable excipient., compared with the pesticidal activity of individual components, is not merely a combination of three actives, but also provides excellent synergistic effect.

The rates of application of the sulphur and of the individual compounds are reduced while retaining an equally good action. Further, the combined mixture also achieves a high degree of pest control where both individual substances have become completely ineffective when excessively low rates are applied. This allows a considerable widening of the spectrum of pests which can be controlled and, on the other hand, an increased safety upon use.

In addition to the actual synergistic action with regard to the pesticidal activity, the compositions according to the invention additionally have other surprising advantages, which can also be termed synergistic in a wider sense: for example, they allow the control of pests which are not, or not sufficiently, controlled by the individual compounds, and the compositions according to the invention are better tolerated by plants, i.e. they are less phytotoxic than the individual compounds. The compositions according to the invention are active against all or individual development stages of normally sensitive, but also resistant to pests. The insecticidal and/or acaricidal action of the compounds according to the invention can become apparent either directly, i.e. by destroying the pests immediately or only after some time has elapsed, for example during an ecdysis, or indirectly, for example by a reduced oviposition rate and/or hatching rate, the good action corresponding to a destruction rate (mortality) of at least 50 to 60%.

With the use of the agrochemical composition the number of applications to control wide range of pests appearing at the same time is minimized, which decreases labour costs. The composition is highly safe to the user and to the environment. The composition offers the user a single homogenous application eliminating the need for tank mix. The composition also is cost-effective, as it provides much greater simultaneous control and can be used in a variety of crops with a broader spectrum of protection. Also, the composition can serve as an intervention application between very specific actives which are likely to lead to resistance in areas of epidemic and high frequency of pesticidal applications.

The various advantageous properties associated with the compositions according to the invention, include but are not limited to: a broadening of the spectrum of pesticidal activity to other pests, for example to resistant strains; adequate control of the pests at a rate of application at which the individual compounds are not very effective, advantageous behaviour during formulating and/or upon application, improved stability, improved toxicological and/or ecotoxicological behaviour, improved crop characteristics including crop yields, more developed root system, increase in plant height, bigger leaf blade, less dead basal leaves, strong tillers, greener leaf colour, less fertilizers needed, increased shoot growth, improved plant vigour, earlier flowering, less plant verse (lodging), and other advantages familiar to a person skilled in the art.

From the foregoing it will be observed that numerous modifications and variations can be effectuated without departing from the true spirit and scope of the novel concepts of the present invention. It is to be understood that no limitation with respect to the specific embodiments illustrated is intended or should be inferred.

EXAMPLES

Example 1

Sulfur 60% +Imidacloprid 1.25%+Lambdacyhalothrin 0.75% WG 60.0 parts of Sulphur,
1.25 parts of Imidacloprid,
0.75 parts of Lambda cyhalothrin,
3 parts of Naphthalene sulfonate condensate (Tammol DN),
6 parts Phenol sulfonate (Tamol NN),
12 parts of Lignin sulfonate (Borresperse),
q.s. of Kaolin

Example 2

Sulfur 22%+Imidacloprid 15%+Lambda-cyhalothrin 9% ZC 22.0 parts of Sulphur,
15 parts of Imidacloprid,
9 parts of Lambda cyhalothrin,
2.0 parts of Naphthalene sulfonate condensate-sodium salt
3.0 parts of Phenol sulfonate condensate-sodium salt
7.0 parts of 2% xanthum gel
5.0 parts of Propylene glycol
0.4 parts of Aminoplast polymer
0.8 parts of Polymeric surfactant
0.8 parts of Alcohol ethoxylate
4.0 parts of C-9 solvent
q.s. Water

Example 3

Sulfur 80%+Acetamiprid 2.0%+Deltamethrin 1.4% WG 80.0 parts of Sulphur,
2.0 parts of Acetamiprid,
1.4 parts of Deltamethrin,
1.5 parts of of Naphthalene sulfonate condensate (Tammol DN),
3.0 parts of Phenol sulfonate (Tamol NN),
7.0 parts of Lignin sulfonate (Borresperse),
q.s. of Kaolin Efficacy Trials Brinjal (*Solanum melongena* L.) is one of the most popular and economically important vegetables crop. Brinjal is attacked by plethora of insect and mite pests starting from seedling stage to senescence. In the light of above fact, a field trial was carried out to assess the efficacy of different combinations of insecticides against pests of brinjal.

Example 1

Evaluation of Efficacy of Combinations of Sulphur+Imidacloprid+Lambda Cyhalothrin The trials were laid out in a randomized block design in Akola district of Maharashtra state in India, The plot size was 9m$^2$ with plant to plant and row to row distance of 15 cm and 30 cm, respectively. All the recommended agronomic practices were followed to grow the crop with thirteen treatments and three replications.

The seedlings were transplanted. Brinjal variety, Arka Nidhi was raised as per recommended package of practices, except insect-pest management practices.

Observations on the total number of thrips and white fly were recorded at one day before first spray and 2$^{nd}$, 3$^{rd}$, 4$^{th}$, 5$^{th}$ and 6$^{th}$ days after spray.

On thrips, all the treatment with combinations of sulphur, imidacloprid and lambda cyhalothrin showed a better efficacy as compared to the treatments with single insecticidal actives (table 1 and 2). Also treatment 4, 5 and 6 showed a synergistic effect when evaluated as per Colby's method as shown in table 2.

On White fly also, all the treatments with the combinations of sulphur, imidacloprid and lambda cyhalothrin showed a better efficacy as compared to the treatments with single insecticidal actives (table 1 and 3). Also treatment 2 and 3 showed a synergistic effect when evaluated as per Colby's method as shown in table 3. The treatment 2 and 3 proved to be effectively managing the population of white fly upto 15$^{th}$ day of spray with 66.67% and 20% inhibition of white fly respectively in comparison to the treatment no. 7, containing combination of Lambdacyhalothrin and imidacloprid showing only 16.67% inhibition of mite at 15$^{th}$ day.

TABLE 1

Trial data for combinations of Sulphur + Imidacloprid + Lambda cyhalothrin

| Sr. No | Treatment | Active ingredient (g/h) | Dosage/ ha (gm) | No of Active stages *Thrips tabaci* (*Thysanoptera: Thripidae*) | | | | | | No of Active stages White fly (*Bemesia tabaci*) | | | | | |
|---|---|---|---|---|---|---|---|---|---|---|---|---|---|---|---|
| | | | | DBS | 2DAS | 3DAS | 4DAS | 5DAS | 6DAS | DBS | 2DAS | 3DAS | 4DAS | 5DAS | 6DAS |
| 1 | Sulphur 60% + Imidacloprid 1.25% + Lambda cyhalothrin 0.75% WG | 1200 + 25 + 15 | 2000 | 5 | 9 | 4 | 6 | 5 | 4 | 5 | 6 | 7 | 2 | 3 | 4 |

TABLE 1-continued

Trial data for combinations of Sulphur + Imidacloprid + Lambda cyhalothrin

| Sr. No | Treatment | Active ingredient (g/h) | Dosage/ ha (gm) | No of Active stages Thrips tabaci (Thysanoptera: Thripidae) | | | | | | No of Active stages White fly (Bemesia tabaci) | | | | | |
|---|---|---|---|---|---|---|---|---|---|---|---|---|---|---|---|
| | | | | DBS | 2DAS | 3DAS | 4DAS | 5DAS | 6DAS | DBS | 2DAS | 3DAS | 4DAS | 5DAS | 6DAS |
| 2 | Sulphur 60% + Imidacloprid 1.25% + Lambda cyhalothrin 0.75% WG | 2400 + 50 + 30 | 4000 | 4 | 13 | 12 | 4 | 4 | 3 | 9 | 6 | 4 | 2 | 3 | 3 |
| 3 | Sulphur 30% + Imidacloprid 1.25% + Lambda cyhalothrin 0.75% ZC | 600 + 25 + 15 | 2000 | 4 | 7 | 4 | 5 | 5 | 2 | 5 | 4 | 2 | 2 | 3 | 4 |
| 4 | Sulphur 30% + Imidacloprid 1.25% + Lambda cyhalothrin 0.75% ZC | 1200 + 50 + 30 | 4000 | 5 | 7 | 5 | 7 | 3 | 5 | 5 | 10 | 3 | 4 | 4 | 5 |
| 6 | Sulphur 22% + Imidacloprid 15% + Lambda cyhalothrin 9% ZC | 102 + 51 + 30.6 | 340 | 4 | 6 | 3 | 4 | 4 | 4 | 4 | 7 | 4 | 4 | 3 | 4 |
| 7 | Sulphur 22% + Imidacloprid 15% + Lambda cyhalothrin 9% ZC | 135 + 67.5 + 40.5 | 450 | 5 | 6 | 4 | 3 | 3 | 4 | 2 | 6 | 2 | 3 | 6 | 4 |
| 8 | Imidacloprid 12.5% + Lambda cyhalothrin 7.5% WG | 25 + 15 | 200 | 7 | 8 | 4 | 8 | 2 | 4 | 6 | 7 | 4 | 3 | 5 | 5 |
| 9 | Imidacloprid 25% Lambda cyhalothrin 15% ZC | 50 + 30 | 200 | 5 | 7 | 7 | 0 | 5 | 3 | 3 | 6 | 5 | 3 | 2 | 3 |
| 10 | Sulphur 80 WG | 2000 | 2500 | 3 | 9 | 4 | 4 | 4 | 6 | 2 | 6 | 3 | 5 | 2 | 5 |
| 11 | Lambda cyhalothrin 5% EC | 30 | 600 | 5 | 5 | 2 | 6 | 6 | 8 | 0 | 5 | 4 | 2 | 4 | 4 |
| 12 | Imidacloprid 17.8 SL | 25 | 140.5 | 5 | 6 | 8 | 5 | 4 | 8 | 0 | 5 | 3 | 3 | 4 | 5 |
| 13 | Control | | | 5 | 5 | 9 | 7 | 5 | 7 | 5 | 4 | 4 | 5 | 5 | 4 |

TABLE 2

Evaluation of efficacy of the combinations of Sulphur + Imidacloprid + Lambda cyhalothrin on thrips by Colby's method.

| Thrips | Sr no | Expected Growth Inhibition (E1 = 100 − E) | 2DAS | 3DAS | 4DAS | 5DAS | 6DAS |
|---|---|---|---|---|---|---|---|
| | | Expected Growth Inhibition calculated by Colby's method for three way combination | −260 | 14.67 | −60 | −70.67 | −412 |
| Observed growth inhibition | 1 | Sulphur 60% (1200 g/ha) + Lambda cyhalothrin 0.75% (15 g/ha) + Imidacloprid 1.25% (25 g/ha) WG | −80 | 20 | −20 | 0 | 20 |
| | 2 | Sulphur 60% (2400 g/ha) + Lambda cyhalothrin 0.75% (30 g/ha) + Imidacloprid 1.25% (50 g/ha) WG | −225 | −200 | 0 | 0 | 25 |
| | 3 | Sulphur 30% (600 g/ha) + Lambda cyhalothrin 0.75% (15 g/ha) + Imidacloprid 1.25 (25 g/ha) ZC | −75 | 0 | −25 | −25 | −50 |
| | 4 | Sulphur 30% (1200 gm/ha) + Lambda cyhalothrin 0.75% (30 gm/ha) + Imidacloprid 1.25 (50 gm/ha) ZC | −40 | 0 | −40 | −40 | 0 |
| | 5 | Sulphur 22% (102 g/ha) + Lambda cyhalothrin 9% (30.6 g/ha) + Imidacloprid 15% (51 g/ha) ZC | −50 | 25 | 0 | 0 | 0 |

TABLE 2-continued

Evaluation of efficacy of the combinations of Sulphur +
Imidacloprid + Lambda cyhalothrin on *thrips* by Colby's method.

| Thrips | Sr no | Expected Growth Inhibition (E1 = 100 − E) | 2DAS | 3DAS | 4DAS | 5DAS | 6DAS |
|---|---|---|---|---|---|---|---|
| | 6 | Sulphur 22% (135 g/ha) + Lambda cyhalothrin 9% (40.5 g/ha) + Imidacloprid 15% (67.5 g/ha) ZC | −20 | 40 | 20 | 20 | 20 |
| | 7 | Lambda cyhalothrin 7.5% + Imidacloprid 12.5% WG (200 g/ha) | −14.28 | 42.85 | −14.28 | 71.42 | 42.85 |
| | 8 | Lambda cyhalothrin 15% + Imidacloprid 25% ZC (200 g/ha) | −40 | −40 | 100 | 40 | 40 |
| | 9 | Sulphur 80DF (1200 g/ha) | 0 | 66.67 | 33.33 | 33.33 | 33.33 |
| | 10 | Imidacloprid 17.8% (20 g/ha) SL | 75 | 75 | 75 | 50 | 50 |
| | 11 | Lambda cyhalothrin 5% (15 g/ha) EC | 75 | 50 | 75 | 75 | 75 |

TABLE 2

Evaluation of efficacy of the combinations of Sulphur +
Imidacloprid + Lambda cyhalothrin on White fly by Colby's method.

| White fly | Sr. no | Expected Growth Inhibition (E1 =100 − E) | 2DAS | 3DAS | 4DAS | 5DAS | 6DAS |
|---|---|---|---|---|---|---|---|
| | | Expected Growth Inhibition calculated by Colby's method for three way combination | −150.01 | 40 | 50 | 46.668 | −66.67 |
| Observed growth inhibition | 1 | Sulphur 60% (1200 g/ha) + Lambda cyhalothrin 0.75% (15 g/ha) + Imidacloprid 1.25% (25 g/ha) WG | −20 | −40 | 60 | 40 | 20 |
| | 2 | Sulphur 60% (2400 g/ha) + Lambda cyhalothrin 0.75% (30 g/ha) + Imidacloprid 1.25% (50 g/ha) WG | 33.33 | 55.56 | 77.78 | 66.67 | 66.67 |
| | 3 | Sulphur 30% (600 g/ha) + Lambda cyhalothrin 0.75% (15 g/ha) + Imidacloprid 1.25 (25 g/ha) ZC | 20 | 60 | 60 | 40 | 20 |
| | 4 | Sulphur 30% (1200 gm/ha) + Lambda cyhalothrin 0.75% (30 gm/ha) + Imidacloprid 1.25 (50 gm/ha) ZC | −100 | 40 | 20 | 20 | 0 |
| | 5 | Sulphur 22% (102 g/ha) + Lambda cyhalothrin 9% (30.6 g/ha) + Imidacloprid 15% (51 g/ha) ZC | 0 | 0 | 0 | 25 | 0 |
| | 6 | Sulphur 22% (135 g/ha) + Lambda cyhalothrin 9% (40.5 g/ha) + Imidacloprid 15% (67.5 g/ha) ZC | −200 | 0 | −50 | −200 | −100 |
| | 7 | Lambda cyhalothrin 7.5% + Imidacloprid 12.5% WG (200 g/ha) | −16.67 | 33.33 | 50 | 16.67 | 16.67 |
| | 8 | Lambda cyhalothrin 15% + Imidacloprid 25% ZC (200 g/ha) | −100 | −66.67 | 0 | 33.33 | 0 |
| | 9 | Sulphur 80DF (1200 g/ha) | −20 | 40 | 0 | 60 | 0 |
| | 10 | Imidacloprid 17.8% (20 g/ha) SL | −66.67 | 0 | 0 | −33.33 | −66.67 |
| | 11 | Lambda cyhalothrin 5% (15 g/ha) EC | −25 | 0 | 50 | 0 | 0 |

Example 2

Evaluation of Efficacy of Combinations of Sulphur+Acetamiprid+Deltamethrin

Brinjal (*Solanum melongena* L.) is one of the most popular and economically important vegetables crop. Brinjal is attacked by plethora of insect and mite pests starting from seedling stage to senescence. The trials were laid out in a randomized block design in Akola district of Maharashtra state in India, having plot size of 4.5 m×4.2 m at our experimental farm with eight treatments and three replications. The seedlings were transplanted. Brinjal variety, Arka Nidhi was raised as per recommended package of practices, except insect-pest management practices. Each row considered as a treatment, 100 plants were tagged for data recording and likewise same for three replications. Single round of spray were given. In the experiment, treatments were imposed after sufficient build up of red spider mites. The pre and post treatment observations on live red spider mite populations were assessed on $3^{rd}$, $7^{th}$, $10^{th}$ and $15^{th}$ days after spray.

All the treatment with combinations of sulphur, acetamiprid and deltamethrin showed a better efficacy as compared to the treatments with single insecticidal actives (table 4 and 5). Also treatment 2 showed synergistic effect when evaluated by Colby's method (Table 5). The treatment 2 proved to be effectively managing the population of mite upto $15^{th}$ day of spray with 90.37% inhibition of mite in comparison to the treatment no.4, containing combination of Acetamiprid and Deltamethrin showing only 31.82% inhibition of mite at $15^{th}$ day.

Example 3

Evaluation of Efficacy of Combinations of Sulphur+Acetamiprid+Lambda Cyhalothrin Brinjal (*Solanum melongena* L.) is one of the most popular and economically important vegetables crop. Brinjal is attacked by plethora of insect and mite pests starting from seedling stage to senescence. The trials were laid out in a randomized block design in Akola district of Maharashtra state in India, having plot size of 4.5 m×4.2 m at our experimental farm with nine treatments and three replications. The seedlings were transplanted. Brinjal variety, Arka Nidhi was raised as per recommended package of practices, except insect-pest management practices.

Bioefficacy of combination of an acaricide with neonicotinoid and synthetic pyrethroid was worked out by selecting Sulphur+Acetamiprid+Lambda cyhalothrin, against white

TABLE 4

Trial data for combinations of Sulphur + Acetamiprid + Deltamethrin

| Sr. No. | Treatments | Active ingredient (g/ha) | Dosage/ ha (gm) | 1 DBS | 3 DAS | 7 DAS | 10 DAS | 15 DAS |
|---|---|---|---|---|---|---|---|---|
| | | | | \multicolumn{5}{c}{Number of immature active stages (*Tefranychus sp.*)/ 4 cm² leaf area} |
| 1 | Sulphur 40% + Acetamiprid 1% + Deltamethrin 0.75% WG | 500 + 100 + 25 | 2000 | 122 | 42 | 36 | 24 | 25 |
| 2 | Sulphur 80% + Acetamiprid 2% + Deltamethrin 1.4% WG | 600 + 100 + 25 | 1000 | 135 | 28 | 12 | 10 | 13 |
| 3 | Sulphur 40% + Acetamiprid 5% + Deltamethrin 3.5% WG | 700 + 85 + 20 | 200 | 102 | 46 | 32 | 27 | 30 |
| 4 | Acetamiprid 10% + Deltamethrin 7% WG | 40 + 20 | 200 | 110 | 75 | 67 | 54 | 62 |
| 5 | Sulphur 80DF | 1200 | 1250 | 104 | 67 | 46 | 22 | 32 |
| 6 | Deltamethrin 2.8% EC | 12.5 | 500 | 80 | 43 | 38 | 40 | 42 |
| 7 | Acetamiprid 20% SP | 20 | 100 | 128 | 96 | 100 | 110 | 124 |
| 8 | Control | | | 121 | 114 | 120 | 115 | 132 |

TABLE 5

Evaluation of efficacy of the combinations of Sulphur + Acetamiprid + Deltamethrin on mite by Colby's method.

| Mite | Sr no | Sulphur + Acetamiprid + Deltamethrin | 3 DAS | 7 DAS | 10 DAS | 15 DAS |
|---|---|---|---|---|---|---|
| | | Expected Growth Inhibition calculated by Colby's method for three way combination | 74.03 | 83.59 | 90.91 | 84.35 |
| Observed growth inhibition | 1 | Sulphur 40% (800 g/ha) + Acetamiprid 1% (20 g/ha) + Deltamethrin 0.75% (14 g/ha)WG | 65.57 | 70.49 | 80.33 | 79.51 |
| | 2 | Sulphur 80% (800 g/ha) + Acetamiprid 2% (20 g/ha) + Deltamethrin 1.4% (14 g/ha) WG | 79.26 | 91.11 | 92.59 | 90.37 |
| | 3 | Sulphur 40% (800 g/ha) + Acetamiprid 5% (20 g/ha) + Deltamethrin 3.5% (14 g/ha) WG | 54.90 | 68.63 | 73.53 | 70.59 |
| | 4 | Acetamiprid 10% (20 g/ha) + Deltamethrin 7% WG (14 g/ha) | 31.82 | 39.09 | 50.90 | 31.82 |
| | 5 | Sulphur 80 DF 96% (1200 g/ha) | 35.58 | 55.77 | 78.85 | 69.23 |
| | 6 | Acetamiprid 20% (20 g/ha) SP | 25 | 21.88 | 14.06 | 3.13 |
| | 7 | Deltamethrin 2.8% (14 g/ha) EC | 46.25 | 52.5 | 50 | 47.5 | fly control over the insecticide used alone and in two way combination of Acetamiprid+Lambda cyhalothrin with an untreated check.

Single sprays of each treatment were applied with the help of knapsack sprayer at fortnightly intervals starting from the advance vegetative phase.

Average number of whitefly population was counted per twing per plant from five randomly selected plants per plot and were recorded at one day before first spray and $3^{rd}$, 7th, 10th and $15^{th}$ days after each spray.

All the treatment with combinations of sulphur, acetamiprid and lambda cyhalothrin showed a better efficacy as compared to the treatments with single insecticidal actives (table 6 and 7). Also treatment 2 and 3 showed synergistic effect when evaluated by Colby's method (Table 7).Treatment 2 and 3 proved to be effectively managing the population of white fly with 100% inhibition on $7^{th}$ day and 93.06% and 93.55% inhibition of white fly at $15^{th}$ day of spray in comparision to treatment no.4, using two way combination of acetamiprid and lambda cyhalothrin, showing only 91.18% inhibition of mite at $15^{th}$ day.

TABLE 6

Trials data for combinations sulphur + Acetamiprid + Lambda cyhalothrin

| Sr. No. | Treatments | Active ingredient (g/ha) | Dosage/ha (gm) | Number of immature active stages (*Bemesia*)/4 cm² leaf area | | | | |
|---|---|---|---|---|---|---|---|---|
| | | | | 1DBS | 3DAS | 7DAS | 10DAS | 15DAS |
| 1 | Sulphur 65% + Acetamiprid 0.7% + Lambda cyhalothrin 0.7% WG | 1300 + 14 + 15 | 2000 | 56 | 4 | 0 | 3 | 6 |
| 2 | Sulphur 25% + Acetamiprid 7% + Lambda cyhalothrin 7.5% ZC | 50 + 14 + 15 | 200 | 72 | 2 | 0 | 1 | 5 |
| 3 | Sulphur 25% + Acetamiprid 10% + Lambda cyhalothrin 10% ZC | 50 + 20 + 20 | 200 | 62 | 0 | 0 | 0 | 4 |
| 4 | Lambda cyhalothrin 7.5% + Acetamiprid 7% WG | 15 + 14 | 200 | 68 | 3 | 0 | 2 | 6 |
| 5 | Sulphur 80DF | 1200 | 1250 | 104 | 67 | 46 | 22 | 32 |
| 6 | Lambda cyhalothrin 5% EC | 15 | 300 | 55 | 10 | 14 | 22 | 32 |
| 7 | Acetamiprid 20% SP | 20 | 100 | 69 | 20 | 18 | 32 | 38 |
| 8 | Control | | | 61 | 74 | 95 | 127 | 142 |

TABLE 7

Evaluation of efficacy of the combinations of sulphur + Acetamiprid + Lambda cyhalothrin on white fly by Colby's method.

| White fly | Sr. no | Expected Growth Inhibition (E1 = 100 − E) | 3DAS | 7DAS | 10DAS | 15DAS |
|---|---|---|---|---|---|---|
| | | Expected Growth Inhibition calculated by Colby's method for three way combination | 96.15 | 96.21 | 95.32 | 91.91 |
| Observed growth inhibition | 1 | Sulphur 65% (1300 g/ha) + Acetamiprid 0.7% (14 g/ha) + Lambda cyhalothrin 0.7% (15 g/ha) WG | 92.86 | 100 | 94.64 | 89.29 |
| | 2 | Sulphur 25% (50 g/ha) + Acetamiprid 7% (14 g/ha) + Lambda cyhalothrin 7.5% (15 g/ha) ZC | 97.22 | 100 | 98.61 | 93.06 |
| | 3 | Sulphur 25% (50 g/ha) + Acetamiprid 10% (14 g/ha) + Lambda cyhalothrin 10% (20 g/ha) ZC | 100 | 100 | 100 | 93.55 |
| | 4 | Acetamiprid 7% (14 g/ha) + Lambda cyhalothrin 7.5% (15 g/ha WG | 95.59 | 100 | 97.05 | 91.18 |
| | 5 | Sulphur 80 DF 96% (1200 g/ha) | 35.58 | 55.77 | 78.85 | 69.23 |
| | 6 | Acetamiprid 20% (20 g/ha) SP | 25 | 21.88 | 14.06 | 3.13 |
| | 7 | Deltamethrin 2.8% (14 g/ha) EC | 46.25 | 52.5 | 50 | 47.5 |

Example 4

Evaluation of Efficacy of Combinations of Sulphur+Thiamethoxam+Lambda Cyhalothrin Brinjal (*Solanum melongena* L.) is one of the most popular and economically important vegetables crop. Brinjal is attacked by plethora of insect and mite pests starting from seedling stage to senescence.

The trials were laid out in a randomized block design in Akola district of Maharashtra state in India, having plot size of 4.5 m×4.2 m at our experimental farm with nine treatments and three replications.

The seedlings were transplanted. Brinjal variety, Arka Nidhi was raised as per recommended package of practices, except insect-pest management practices.

Bioefficacy of combination of an acaricide with neonicotinoid and synthetic pyrethroid was worked out by selecting Sulphur+Thiamethoxam+Lambda c yhalothrin, against the shoot and fruit borer over the insecticide used alone and in two way combination of Thiamethoxam+Lambda cyhalothrin with an untreated check.

The pest, Shoot and fruit borer, *Leucinodes orbonalis* found to cause severe damage and loss to brinjal. The larvae bore into tender shoots in the early stage resulting in drooping shoots, which are readily visible in the infested fields. At the later stage, caterpillars bore into flower buds and fruits also.

Single sprays of each treatment were applied with the help of knapsack sprayer at fortnightly intervals starting from the fruit initiation. Each row considered as a treatment, 100 plants were tagged for data recording and likewise same for three replications.

Observations on the total number of drooping shoots and larvae observed per plot, percent shoot infestation from five randomly selected plants and percent fruit infestation by *L. orbonalis* on weight basis per plot were recorded at one day before first spray and $3^{rd}$, 7th, $10^{th}$ and $15^{th}$ days after each spray.

All the treatment with combinations of sulphur, thiamethoxam and lambda cyhalothrin showed a better efficacy as compared to the treatments with single insecticidal actives (table 8 and 9). As it can be seen from table 8, the treatment 1 and 2 provides good control over the population of shoot & fruit borer till 15th Days of spray, whereas in case of used alone as can be seen in treatment no. 5, the similar trend of control can be noticed but the synergistic effect of combination proves to be better in persistence of the product within the plant body, due to which the population does not increase in the way it is noticed when used alone.

Also treatment 1 and 2 showed synergistic effect when evaluated by Colby's method (Table 9).The treatment 1 and 2 proved to be effectively managing the population of shoot & fruit borer with 78.26% and 87.5% inhibition respectively on 3rd day and 95.65% and 95.83% inhibition respectively on $15^{th}$ day in comparison to treatment no. 3, containing a combination of thiamethoxam and lambda cyhalothrin, showing only 82.14% inhibition of population of shoot & fruit borer at $3^{rd}$ day and 92.85% at $15^{th}$ Day.

TABLE 8

Trial data for combinations sulphur + Thiamethoxam + Lambda cyhalothrin

| Sr. No. | Treatments | Active ingredient (g/ha) | Dosage/ha (gm) | % Shoot infection days after spray 1 DBS | 3 DAS | 7 DAS | 10 DAS | 15 DAS |
|---|---|---|---|---|---|---|---|---|
| 1 | Sulphur 60% + Lambda cyhalothrin 1% + Thiamethoxam 2.5% WG | 1200 + 20 + 50 | 2000 | 30 | 15 | 5 | 2 | 3 |
| 2 | Sulphur 25% + Lambda cyhalothrin 10% + Thiamethoxam 12.5% ZC | 50 + 20 + 25 | 200 | 24 | 3 | 0 | 0 | 1 |
| 3 | Lambda cyhalothrin 9.6% + Thiamethoxam 12.8 ZC | 19.2 + 25.6 | 200 | 28 | 5 | 2 | 0 | 2 |
| 4 | Sulphur 80DF | 1200 | 1250 | 23 | 25 | 28 | 33 | 35 |
| 5 | Lambda cyhalothrin 5% EC (15 g/ha) | 15 | 300 | 30 | 10 | 0 | 2 | 7 |
| 6 | Thiamethoxam 25% | 50 | 200 | 25 | 20 | 18 | 20 | 22 |
| 7 | Control | | | 28 | 34 | 35 | 37 | 42 |

TABLE 9

Evaluation of efficacy of the combinations of Sulphur + Thiamethoxam + Lambda cyhalothrin on Fruit and shoot borer by Colby's method.

| Fruit and shoot borer | Sr. no | Expected Growth Inhibition (E1 = 100 − E) | 3 DAS | 7 DAS | 10 DAS | 15 DAS |
|---|---|---|---|---|---|---|
| | | Expected Growth Inhibition calculated by Colby's method for three way combination | 71.01 | 100 | 92.35 | 68.75 |
| Observed growth inhibition | 1 | Sulphur 60% (1200 g/ha) + Lambda cyhalothrin 10% (20 g/ha) + Thiamethoxam (50 g/ha) 2.5% WG | 78.26 | 92.75 | 97.10 | 95.65 |
| | 2 | Sulphur 25% (1200 g/ha) + Lambda cyhalothrin 10% (20 g/ha) + Thiamethoxam 12.5% (25 g/ha) ZC | 87.5 | 100 | 100 | 95.83 |

TABLE 9-continued

Evaluation of efficacy of the combinations of Sulphur + Thiamethoxam + Lambda cyhalothrin on Fruit and shoot borer by Colby's method.

| Fruit and shoot borer | Sr. no | Expected Growth Inhibition (E1 = 100 − E) | 3 DAS | 7 DAS | 10 DAS | 15 DAS |
|---|---|---|---|---|---|---|
| | 3 | Lambda cyhalothrin 9.6% (19.2 g/ha) + Thiamethoxam (25.2 g/ha) 12.8 ZC | 82.14 | 92.87 | 100 | 92.85 |
| | 4 | Sulphur 80DF (1200 g/ha) | −8.70 | −21.74 | −43.48 | −52.17 |
| | 5 | Thiamethoxam 25% (50 g/ha) | 20 | 28 | 20 | 12 |
| | 6 | Lambda cyhalothrin 5% EC (15 g/ha) | 66.67 | 100 | 93.33 | 76.67 |

I claim:

1. An agricultural composition comprising sulphur in the range from 20% to 80% of the total composition, a chloronicotinyl compound in the range from 0.7% to 25% of the total composition, a pyrethroid compound in the range from 0.75% to 10% of the total composition and at least one agrochemically acceptable excipient.

2. The agricultural composition of claim 1, wherein the chloronicotinyl compound is selected from the group comprising of acetamiprid, thiamethoxam, imidacloprid, thiacloprid, dinetofuran, and chlothianidin or salts thereof.

3. The agricultural composition of claim 1, wherein the pyrethroid compound is selected from the group comprising of acrinathrin, bifenthrin, cyfluthrin, cypermethrin, cyhalothrin, deltamethrin, fenvalerate, fenpropathrin and lambda cyhalothrin or salts thereof.

4. The pesticidal composition of claim 1, wherein the chloronicotinyl compound is imidacloprid and the pyrethroid compound is lambda cyhalothrin.

5. The pesticidal composition of claim 1, wherein the chloronicotinyl compound is acetamiprid and the pyrethroid compound is deltamethrin.

6. The pesticidal composition of claim 1, wherein the chloronicotinyl compound is acetamiprid and the pyrethroid compound is lambda cyhalothrin.

7. The pesticidal composition of claim 1, wherein the chloronicotinyl compound is thiamethoxam and the pyrethroid compound is lambda cyhalothrin.

8. The agricultural composition of claim 1, wherein the composition is in the form of one of water dispersible granules or pellets, wettable powders, dusting powders, suspension concentrates, emulsion concentrates, suspo-emulsions, microemulsions, capsulated suspension, emulsions for seed treatment or combinations thereof.

* * * * *